United States Patent
Addison et al.

(10) Patent No.: US 9,433,534 B2
(45) Date of Patent: Sep. 6, 2016

(54) PATTERNED SILICONE COATING

(75) Inventors: Deborah Addison, Keasden (GB); Sally Stephens, Skipton (GB); Risham Amjad, Manchester (GB); Patrick Brosnan, West Yorkshire (GB); Gary Street, West Yorkshire (GB); Ian Teet, Kelbrooke (GB)

(73) Assignee: KCI USA, INC., San Antonio, TX (US)

( * ) Notice: Subject to any disclaimer, the term of this patent is extended or adjusted under 35 U.S.C. 154(b) by 190 days.

(21) Appl. No.: 14/111,626

(22) PCT Filed: Apr. 13, 2012

(86) PCT No.: PCT/GB2012/050822
§ 371 (c)(1),
(2), (4) Date: Jan. 23, 2014

(87) PCT Pub. No.: WO2012/140441
PCT Pub. Date: Oct. 18, 2012

(65) Prior Publication Data
US 2014/0171851 A1  Jun. 19, 2014

(30) Foreign Application Priority Data

Apr. 15, 2011 (GB) .................................. 1106491.2

(51) Int. Cl.
*A61F 13/02* (2006.01)
*B05D 1/28* (2006.01)
*C09J 5/06* (2006.01)

(52) U.S. Cl.
CPC ......... *A61F 13/025* (2013.01); *A61F 13/0276* (2013.01); *A61F 13/0283* (2013.01); *B05D 1/28* (2013.01); *C09J 5/06* (2013.01); *Y10T 428/24802* (2015.01)

(58) Field of Classification Search
CPC ....... A61F 13/00; A61F 13/02; A61L 15/01; A61L 15/16; B07B 1/49; A61K 9/70
USPC .......................................... 424/443; 209/399
See application file for complete search history.

(56) References Cited

U.S. PATENT DOCUMENTS

| 5,641,506 A * | 6/1997 | Talke ................. A61B 10/0035 424/443 |
| 2002/0130064 A1* | 9/2002 | Adams ................. B01D 29/012 209/399 |
| 2005/0233072 A1 | 10/2005 | Stephan et al. |

FOREIGN PATENT DOCUMENTS

| EP | 0251810 | * | 7/1986 | ............. A61L 15/01 |
| EP | 0251810 A2 | | 1/1988 | |

(Continued)

OTHER PUBLICATIONS

International Search Report (PCT/GB2012/050822) dated Aug. 8, 2012 3 pages.

*Primary Examiner* — Dah-Wei D Yuan
*Assistant Examiner* — Andrew Bowman (57) ABSTRACT

A method of applying a patterned coating of a silicone adhesive to a substrate sheet, comprising the steps of pattern coating a silicone precursor composition onto the substrate, followed by thermally curing the precursor composition coated on the substrate. The precursor composition is a viscous fluid, and the pattern coating is performed by suitably modified block printing, intaglio printing or screen printing methods. Also provided are coated substrates obtainable by the methods of the invention, and wound dressings comprising such coated substrates.

9 Claims, 3 Drawing Sheets

(56) References Cited

FOREIGN PATENT DOCUMENTS

| GB | 2425487 A | | 11/2006 | |
|----|-----------|---|---------|---|
| WO | WO9622753 | * | 8/1996 | ............. A61F 13/00 |
| WO | 2009/081134 A1 | | 7/2009 | |
| WO | 2012/140441 A1 | | 10/2012 | |

* cited by examiner

PATTERNED SILICONE COATING

The present invention relates to methods of providing patterned coatings of silicone adhesives on sheet-like substrates, in particular on medical substrates such as wound dressings.

Silicone pressure-sensitive adhesives are known for use in medical products such as wound dressings. The silicone adhesives have high medical acceptability and are capable of being sterilized by conventional methods such as autoclaving, gamma and ethylene oxide without loss of properties. A drawback of the silicone adhesives is that they have limited oxygen and moisture permeability. This means that a continuous coating of the silicone adhesive on, for example, a wound dressing backing sheet, results in poor breathability of the resulting wound dressing. It is therefore desirable to provide a discontinuous silicone adhesive layer to maintain breathability of the dressing.

Soft silicone adhesives are prepared from a fluid polymerizable precursor mixture that is coated onto a substrate, for example by dip-coating or coating process, followed by thermal curing. The precursor composition is desirably a solventless composition. The resulting soft silicone adhesives are generally soft and tacky, but generally solvent free, and therefore readily repositionable on the skin.

Hitherto, discontinuous silicone adhesive layers have been provided by coating the silicone adhesive precursor onto an open mesh substrate, such as a gauze, so that the apertures of the substrate remain open after coating with the precursor, followed by curing of the coated substrate. The resulting silicone adhesive-coated, open mesh structure can then be applied to a suitable substrate such as a semipermeable wound dressing backing sheet. Coated mesh silicone adhesive structures of this type are described, for example, in EP-A-0251810.

US-A-20050233072 describes a method of applying a pattern coating of hydrogel forming polymer onto a substrate, comprising moving the substrate through a slot coater that applies a patterned coating of a low-viscosity polymerizable and/or crosslinkable polymer precursor material to the substrate, followed by polymerizing the coating downstream of the coater.

However, it has not previously been suggested to pattern coat a silicone adhesive directly onto a substrate such as a backing sheet. This may be because the silicone adhesive precursor is viscous and solvent-free, and therefore cannot be used in conventional pattern coating methods such as screen printing or slot coating. Furthermore, silicone compositions are generally incompatible with common hydrophilic wound dressing materials, whereby they adhere relatively weakly to such materials unless a primer coating is applied between the substrate and the silicone adhesive. This further hinders conventional pattern coating with silicone adhesives.

In a first aspect, the present invention provides a method of applying a patterned coating of a silicone adhesive to a substrate sheet, comprising the steps of pattern coating a silicone precursor composition onto the substrate, followed by thermally curing the precursor composition coated on the substrate.

In a first embodiment, the step of pattern coating is performed by the steps of coating the silicone prepolymer composition onto an apertured support layer having holes and lands to provide a coated apertured support layer, followed by applying the coated support layer to the substrate sheet, followed by removing the coated apertured support layer to leave a patterned layer of the silicone composition on the substrate sheet. This method results in a pattern of the silicone on the substrate sheet that substantially corresponds to the pattern of lands on the support layer. The support layer may be removed before or after the step of curing the silicone.

In a second embodiment, the step of pattern coating is performed by providing a mold having a base surface and recesses in said surface corresponding to the desired adhesive pattern, filling said recesses with said silicone prepolymer composition, applying said substrate sheet to said base surface so that it contacts the prepolymer mixture in the recesses, curing said prepolymer mixture in contact with the substrate sheet, and removing the substrate sheet and silicone layer from the mold. In other words, this embodiment covers various forms intaglio printing of the silicone prepolymer onto the substrate. The pattern of recesses can be connected to form a connected layer of the silicone with apertures, or the recesses may be separated from each other on the surface of the mold so that separate areas of silicone are deposited on the support sheet. The process may be carried out in discontinous fashion using a plurality of flat molds, or in continuous fashion using an intaglio roller.

In a third embodiment, the method comprises providing a mold sheet having upper and lower surfaces and a pattern of apertures extending between the upper and lower surfaces, filling the apertures with the fluid silicone prepolymer composition, contacting one of said upper or lower surfaces with the support sheet so that said support sheet contacts said fluid silicone prepolymer composition in said apertures, curing the silicone prepolymer composition in contact with the support sheet, and removing the mold sheet. The step of curing may be carried out before or after the step of curing. This method resembles screen printing, but the apertures in the mold sheet are substantially larger than the apertures conventionally used for printing screens so that the viscosity of the silicone precursor does not hinder printing. The process may be carried out in discontinuous fashion using a plurality of flat mold sheets, or in continuous fashion using an apertured roller as described in more detail below.

The invention will now be described in more detail with reference to the accompanying drawings, in which.

As noted above, in a first aspect the present invention provides a method of applying a patterned coating of a silicone adhesive to a substrate sheet, comprising the steps of pattern coating a silicone precursor composition onto the substrate, followed by curing the precursor composition coated on the substrate.

The pattern of silicone adhesive may be any regular or irregular pattern. In certain embodiments the pattern has translational symmetry along at least one axis, for example along two or three axes. In certain embodiments, the pattern is in the form of a network of adhesive coating, such as a mesh pattern or a honeycomb pattern. In other embodiments the pattern consist of a plurality of islands, dots, or patches of adhesive separated by adhesive-free regions of the substrate. In yet other embodiments, the pattern may be in the form of an adhesive-coated margin or annulus surrounding an adhesive-free area, for example for the production of adhesive-bordered dressings. In any event, the adhesive pattern suitably covers from about 10% to about 90% of the area of the coated surface of the substrate, for example from about 20% to about 50% of said area. The patterning of the adhesive is macroscopic, for example the minimum width dimension of any coated area is suitably greater than about 2 mm. The density of the coating is suitably from about 20 gsm to 350 gsm, more suitably from about 30 gsm to about 250 gsm.

The substrate sheet suitably provides a protective covering, cushioning, mechanical support and/or liquid absorbency, for example in a wound dressing. Suitably, the substrate sheet is formed from a material that is hydrophilic, suitably a material that does not swell or dissolve significantly in water or wound fluid. Suitably, the substrate sheet has an uncompressed thickness of from about 0.2 mm to about 15 mm, for example from about 0.5 mm to about 5 mm.

The substrate sheet may be any of the layers conventionally used to form layers over a wound contacting layer in a laminated wound dressing, for example absorbent layers or backing layers. In certain embodiments, the substrate sheet is a backing layer in the form of a sheet of continous semipermeable or impermeable polymer. In other embodiments the substrate sheet may be an absorbent layer for example a hydrophilic foam, a sponge, a film, or a textile layer. The textile may be nonwoven, knitted or woven.

The curing of the silicone prepolymer in situ achieves strong bonding between the silicone adhesive and substrate sheet surfaces that are normally incompatible with and non-adherent to silicone, including hydrophilic surfaces such as polyurethane or hydrocolloid surfaces. This bonding is suitably achieved without the use of a silicone primer to improve adhesion, i.e. it is direct bonding between the silicone and the material of the substrate sheet.

In particular embodiments, the substrate sheet is (a) a semipermeable or impermeable polymer film, or (b) a hydrophilic foam sheet, or (c) a nonwoven web.

Suitable semipermeable or impermeable polymer films for the substrate sheet include any of the semipermeable films conventionally used to form a backing sheet of wound dressings. The films are suitably continuous, i.e. they do not comprise macroscopic apertures that would allow passage of wound fluid. Suitably, the substrate sheet in these embodiments is also microorganism-impermeable. Suitable continuous conformable substrate sheets of this type will suitably have a moisture vapor transmission rate (MVTR) of the substrate sheet alone of 300 to 35000 g/m$^2$/24 hrs, suitably 500 to 25000 g/m$^2$/24 hrs at 37.5° C. at 100% to 10% relative humidity difference (measured before coating with the silicone adhesive). It has been found that such moisture vapor transmission rates allow the wound under the dressing to heal under moist conditions without causing the skin surrounding the wound to macerate. The substrate sheet thickness in these embodiments is suitably in the range of 10 to 1000 micrometers, more suitably 100 to 500 micrometers.

Suitable polymers for forming the substrate sheet in these embodiments include polyurethanes and poly alkoxyalkyl acrylates and methacrylates. Suitably, the substrate sheet in these embodiments comprises a continuous layer of a high density blocked polyurethane foam that is predominantly closed-cell. A suitable backing sheet material is the polyurethane film available under the Registered Trade Mark ESTANE 5714F. Also suitable are elastomeric polymeric esters such as Du Pont HYTREL (Registered Trade Mark).

Suitable hydrophilic foam sheets for use as the substrate sheet include polyurethane foams, carboxylated butadiene-styrene rubber, polyacrylate, polyvinylic or cellulosic foams. The hydrophilic foam may be open-cell or closed-cell. Suitably, the foam comprises a polyurethane, and more suitably it comprises at least 50% by weight of one or more polyurethanes, for example at least 75% by weight thereof.

The hydrophilic polyurethane foam materials are foamed by reacting particular diisocyanates or isocyanate-capped prepolymers with suitable chain extending compounds having amine and/or alcohol multiple functionality. Chain terminating compounds such as mono-amines or monohydric alcohols may be included in the reaction mixture. Water may be included in the reaction mixture, since it reacts with isocyanate to liberate carbon dioxide for foaming the mixture.

The hydrophilic foams used in the substrate sheets of the invention may also have the property of swelling and expanding when water is absorbed. The degree of swelling of the hydrophilic foams on complete saturation with an aqueous medium is typically at least 100% (expressed in terms of increase in volume), and suitably at least 200%. Preferred foams swell by 400 to 800%. Despite this high degree of swelling, however, the foams of the invention retain their integrity even after absorption of large quantities of water. Typically, the cells of the hydrophilic foams have an average diameter in the range 0.1 to 0.6 mm. Suitably hydrophilic foams are as described in EP-A-0541391. These foam layers are available from Systagenix Wound Management under the Registered Trade Marks TIELLE and HYPOL.

Suitably, the basis weight of the hydrophilic foam when used as a substrate sheet in the materials of the present invention is from 0.2 to 1.5 kg/m$^2$, more suitably 0.5 to 1.0 kg/m$^2$.

Suitable textiles for use as the substrate sheet include any of those conventionally used for absorbent products, including cellulose woven or nonwoven webs, or cellulose derivatives such as viscose, rayon or oxidized regenerated cellulose. In certain embodiments, the fabric comprises at least about 10 wt. % of hydrogel-forming absorbent fibers based on the dry weight of the fabric, for example, the fabric comprises at least about 20 wt. % of the hydrogel-forming fibers, for example from about 30 wt. % to about 50 wt. % of such fibers.

The telln "hydrogel-forming fibers" refers to fibers that can absorb at least about twice their own weight of water, suitably at least about four times their own weight of water, to form a hydrogel. The fibers are normally insoluble in water. Suitable materials for the hydrogel-forming fibers include alginates, carboxymethylcelluloses, hydroxyethylcelluloses, polyacrylates, and hyaluronates. Suitable materials are calcium alginate and sodium carboxymethylcellulose and mixtures thereof.

Suitably, the fabric comprises at least about 10 wt. % based on the dry weight of the fabric of substantially non-water-absorbent textile fibers, and suitably it comprises at least about 20 wt. % of such fibers, for example from about 30 wt. % to about 60 wt. % of such fibers. Suitable non-absorbent textile fibers include polyamide fibers such as nylon fibers, polyolefin fibers, and viscose fibers.

In some embodiments, the absorbent layer is similar to those described in WO03/053584. That is to say, the absorbent layer comprises or consists essentially of a nonwoven fabric made up of a mixture of from about 10 wt. % to about 90 wt. % of hydrogel-forming absorbent fibers and from about 90 wt. % to about 10 wt. % of non-absorbent textile fibers. In certain embodiments, at least some of the non-absorbent textile fibers are coated with metallic silver ($Ag^0$) as an antimicrobial agent. Suitably, the amount of silver in the fabric is from about 0.1% to about 10 wt. %, based on the dry weight of the fabric. Textiles of this kind are available from Systagenix Wound Management under the Registered Trade Mark SILVERCEL.

The basis weight of the textile substrate sheet may be in the range of 50-500 $g/m^2$, such as 100-400 $g/m^2$. The uncompressed thickness of the textile layer may be in the range of from 0.5 mm to 10 mm, such as 1 mm to 4 mm. The free (uncompressed) liquid absorbency measured for physiological saline may be in the range of 5 to 30 g/g at 25° C.

Suitably, the silicone precursor composition is substantially or completely solvent-free. For example, the precursor composition may comprise less than about 10 wt. % of solvent, typically less than about 1 wt. % of solvent. The term "solvent" is used in its usual sense, that is to say organic and/or aqueous liquid solvents or diluents that do not form part of the final adhesive polymer composition. Suitably, the precursor composition is a viscous fluid, for example a fluid having a viscosity of at least about 1 Pa s, typically about 2 Pa s to about 20 Pa s at 20° C.

Suitably, the silicone composition is a so-called soft skin adhesive silicone elastomer. Such silicones can be made by an addition reaction (hydrosilylation) between (a) a vinyl functional polydimethyl siloxane, such as bis-dimethyl vinyl PDMS, and (b) a hydrogen functional siloxane, such as dimethyl, methylhydrogen siloxane copolymers, hydrogen dimethylsiloxy terminated PDMS. The cure reaction is catalyzed by a hydrosilylation catalyst, such as a noble metal catalyst, suitably a platinum catalyst. Suitably the silicone prepolymer composition further comprises a polymerization inhibitor that is evaporated from said composition during said step of thermally partially curing, for example 2-methyl-3-butyn-2-ol. The polymerization inhibitor is suitably present in an amount of from about 0.001 wt. % to about 1 wt. %, for example from about 0.01 wt. % to about 0.1 wt. % before curing.

Silicone skin adhesive compositions are suitably supplied as two-part systems: Part A contains at least the vinyl prepolymer and the catalyst, while Part B contains the vinyl prepolymer and the SiH siloxane cross linker. The components are mixed immediately before use, optionally with addition of the polymerization inhibitor, to form the adhesive precursor composition.

In embodiments, the silicone coating composition comprises or consists essentially of the following components:

(A) a diorganopolysiloxane having at least 2 alkenyl groups in each molecule;

(B) an organohydrogenpolysiloxane having at least 2 silicon-bonded hydrogen atoms in each molecule, in a quantity sufficient for the ratio between the number of moles of silicon-bonded hydrogen atoms in this component and the number of moles of alkenyl groups in component (A) to have a value of from about 0.6:1 to about 20:1, (C) optionally a platinum group metal catalyst suitably in a quantity providing 0.1 to 500 weight parts as platinum group metal per 1,000,000 weight parts component (A); and (D) a volatile polymerization inhibitor, suitably selected from: alkyne alcohols such as 2-methyl-3-butyn-2-ol, 3,5-dimethyl-1-hexyn-3-ol, and phenylbutynol; ene-yne compounds such as 3-methyl-3-penten-1-yne and 3,5-dimethyl-3-hexen-1-yne; tetramethyltetrahexenyl-cyclotetrasiloxane; and benzotriazole.

The diorganopolysiloxane, component (A), used in the instant invention is the base component of the total composition. This diorganopolysiloxane must contain at least 2 alkenyl groups in each molecule in order for this composition to cure into a rubbery elastic silicone rubber coating composition.

The diorganopolysiloxane (A) comprises essentially straight-chain organopolysiloxane with the average unit formula $R_nSiO_{(4-n)/2}$, wherein R is selected from substituted and unsubstituted monovalent hydrocarbon groups and n has a value of 1.9 to 2.1. R may be exemplified by alkyl groups such as methyl, ethyl, propyl, and others; alkenyl groups such as vinyl, allyl, and others; aryl groups such as phenyl, and others; and haloalkyl groups such as 3,3,3-trifluoropropyl and others. The diorganopolysiloxane (A) should have a viscosity at 25° C. of at least 100 centipoise (1 d Pa·S). When such factors as the strength of the silicone rubber coating membrane, and blendability are taken into account, the viscosity of diorganopolysiloxane (A) at 25° C. is preferably from 1,000 centipoise (1 Pa·S) to 100,000 centipoise (100 Pa·S). The diorganopolysiloxane (A) may be exemplified by dimethylvinylsiloxy-endblocked dimethylpolysiloxanes, dimethylvinylsiloxy-endblocked dimethylsiloxane-methylvinylsiloxane copolymers, and dimethylvinyl-siloxy-endblocked dimethylsiloxane-methylphenylsiloxane copolymers.

Component (B), an organopolysiloxane that contains at least 2 silicon-bonded hydrogen atoms in each molecule, is a crosslinker for the composition of the instant invention. The organopolysiloxane (B) may be exemplified by trimethylsiloxy-endblocked methylhydrogenpolysiloxanes, trimethylsiloxy-endblocked dimethylsiloxanemethylhydrogen-siloxane copolymers, dimethylphenylsiloxy-endblocked methylphenylsiloxanemethyl-hydrogensiloxane copolymers, cyclic methylhydrogenpolysiloxanes, and copolymers that contain the dimethylhydrogensiloxy unit and SiO4/2 unit. The organohydrogenpolysiloxane (B) should be added in a quantity that the ratio between the number of moles of silicon-bonded hydrogen atoms in this organohydrogenpolysiloxane and the number of moles of alkenyl groups in component (A) has a value of 0.6:1 to 20:1.

The platinum group metal catalyst, component (C), used in the compositions is a curing catalyst. The platinum group metal catalyst (C) may be exemplified by platinum micropowder, platinum black, chloroplatinic acid, platinum tetrachloride, olefin complexes of chloroplatinic acid, alcohol solutions of chloroplatinic acid, complexes between chloroplatinic acid and alkenylsiloxanes, rhodium compounds, and palladium compounds. The platinum group metal catalyst (C) should be added generally at 0.1 to 500 weight parts as platinum group metal per 1,000,000 weight parts component (A), and is preferably used at 1 to 50 weight parts as platinum group metal per 1,000,000 weight parts component (A). The reaction will not develop adequately at less than 0.1 weight parts, while additions in excess of 500 weight parts are uneconomical.

The step of curing the silicone adhesive precursor normally comprises thermal curing to at least partially cure the silicone. The thermal curing is suitably performed continuously by passing the coated substrate through an oven. Suitable thermal curing conditions include exposure to a temperature of from about 80° C. to about 200° C., for example about 120° C. to about 180° C. for a time of from about 1 minute to about 10 minutes, for example about 1.5 minutes to about 5 minutes. Especially suitable conditions are 110°-150° C. for 2 to 6 minutes. The elevated temperature results in evaporation of the polymerization inhibitor (when present) from the silicone composition and therefore in polymerization of the silicone. The resulting material is chemically polymerized and dimensionally stable, but may be capable of further curing by ionizing radiation as explained further below.

The thermally cured material may then be subjected to a final cure with ionizing radiation. The ionizing radiation is suitably selected from e-beam radiation and gamma radiation. A variety of procedures for E-beam and gamma ray curing are well-known. The cure depends on the specific equipment used, and those skilled in the art can define a dose calibration model for the specific equipment, geometry, and line speed, as well as other well understood process parameters. The final cure may form part of the final sterilization by irradiation of the products of the invention. Suitably, the method of the invention further comprises the step of packaging the material in a microorganism-impermeable container prior to the step of further curing with ionizing radiation, whereby the step of further curing also sterilizes the material.

Commercially available electron beam generating equipment is readily available. For example, a Model CB-300 electron beam generating apparatus (available from Energy Sciences, Inc. (Wilmington, Mass.). Generally, a support film (e.g., polyester terephthalate support film) runs through a chamber. Generally, the chamber is flushed with an inert gas, e.g., nitrogen while the samples are e-beam cured. Multiple passes through the e-beam sterilizer may be needed.

Commercially available gamma irradiation equipment includes equipment often used for gamma irradiation sterilization of products for medical applications. Cobalt 60 sources are appropriate. Total absorbed doses are suitably from 20 to 60 kGy, more suitably from about 35 to 50 kGy and dose rates are suitably about 7 to 8 kGy/hour.

The step of further curing with ionizing radiation is also effective to bond the silicone adhesive more strongly to the surface of the substrate layer. This is thought to be due to the ionizing radiation forming covalent bonds between the silicone and the substrate layer material.

The final cured silicone adhesive coating is suitably gel- or elastomer-like, substantially hydrophobic, and moderately adherent (tacky). This coating is therefore suitable for direct application to and removal from wounds without excessive trauma, and/or for repositionable application to skin.

In a first embodiment, the step of pattern coating is performed by the steps of coating the silicone prepolymer composition onto an apertured support layer having holes and lands to provide a coated apertured support layer, followed by applying the coated support layer to the substrate sheet, followed by removing the coated apertured support layer to leave a patterned layer of the silicone composition on the substrate sheet. This method results in a pattern of the silicone on the substrate sheet that substantially corresponds to the pattern of lands on the support layer. Thus, the method resembles block printing in that the coated apertured support layer is used as a printing block to print a pattern of silicone prepolymer onto the substrate.

The support layer may be removed before or after the step of curing the silicone. Suitably, the support layer has a surface that is relatively non-adherent to the silicone adhesive, for example a perfluorocarbon surface.

Figure 1:
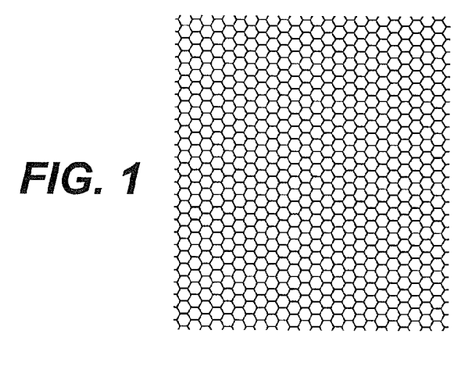
FIG. 1 shows a mesh suitable for use as a support layer in the block printing embodiments according to the present invention.

The support layer may be a mesh or web or fabric suitably formed from a woven, nonwoven or knitted textile, or it may be a molded mesh, or it may be an apertured continuous film. A typical perforated plastic sheet substrate layer is shown in FIG. 1.

The size and shape of the apertures in the support layer generally correspond to the desired adhesive-free areas of the silicone coated substrate. The apertures generally have an aspect ratio of from 1:1 to 5:1, and preferably from 1:1 to 2:1. For example, the apertures may be approximately circular or approximately square. The apertures suitably have an average diameter of from about 2 to about 4 mm, and more suitably from about 3 to about 5 mm. The open area of the support may for example be from about 30% to about 90%, for example from about 50% to about 80%.

The support sheet is suitably foamed from any medically acceptable material, such as cellulose, polyolefins, polyesters, or polyamides.

The support sheet is coated with the silicone adhesive prepolymer composition by any suitable means, such as dip-coating or roller coating. Air or another gas may be blown through the coated support to ensure that the apertures are open before applying the coated support to the substrate. The support sheet is suitably then lifted off the substrate to leave a pattern of silicone adhesive prepolymer on the substrate, which is then cured. In other embodiments, the curing is carried out with the support sheet on the substrate, followed by lifting the support sheet off the cured silicone. The latter embodiments require, of course, that the cured silicone adhesive is less adherent to the support than to the substrate.

In a second embodiment, the step of pattern coating is performed by providing a mold having a base surface and recesses in said surface corresponding to the desired adhesive pattern, filling said recesses with said silicone prepolymer composition, applying said substrate sheet to said base surface so that it contacts the prepolymer mixture in the recesses, curing said prepolymer mixture in contact with the substrate sheet, and removing the substrate sheet and silicone layer from the mold. In other words, this embodiment covers various faints intaglio printing of the silicone prepolymer onto the substrate.

The pattern of recesses can be connected to form a connected layer of the silicone with apertures, or the recesses may be separated from each other on the surface of the mold so that separate areas of silicone are deposited on the support sheet. The depth of the recesses is suitably from about 0.1 mm to about 2 mm, for example about 0.2 mm to about 1 mm. The mold is suitably formed from metal or polymer.

The recesses are suitably filled with the silicone prepolymer composition by flooding the mold with the prepolymer composition, followed by wiping with e.g. a doctor blade to remove the prepolymer from the base surface of the mold outside the recesses. Curing of the prepolymer is performed after printing, as described above.

Figure 2:
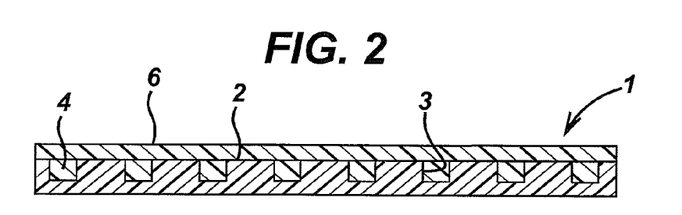
FIG. 2 shows a flat mold suitable for use in a batch intaglio printing method according to the present invention.

The process may be carried out in discontinous fashion using a plurality of flat molds, or in continuous fashion using an intaglio roller. A suitable flat mold is shown in FIG. 2. The mold 1 is formed of polytetrafluoroethylene, and comprises a flat base surface 2 having recesses 3 formed therein by any suitable method such as injection molding or machining. The recesses 3 in this embodiment have substantially constant depth of about 0.5 mm. The recesses 3 are filled with the silicone prepolymer composition 4 by flooding the mold with the prepolymer composition, followed by wiping the base surface 2 with a doctor blade (not shown) to remove excess prepolymer. Substrate layer 6 is laid on top of the base surface 2, optionally with application of pressure, and is then peeled away to provide the substrate layer having a patterned silicone adhesive prepolymer thereon. Curing is then carried out.

Figure 3:
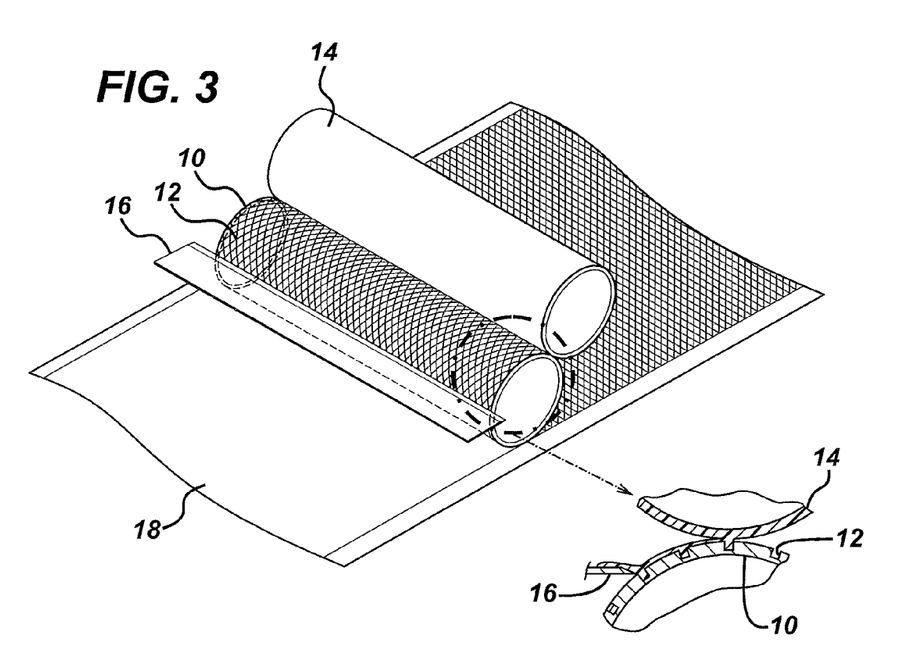
FIG. 3 shows a schematic view of a roller intaglio printing method according to the present invention.
Figure 4:
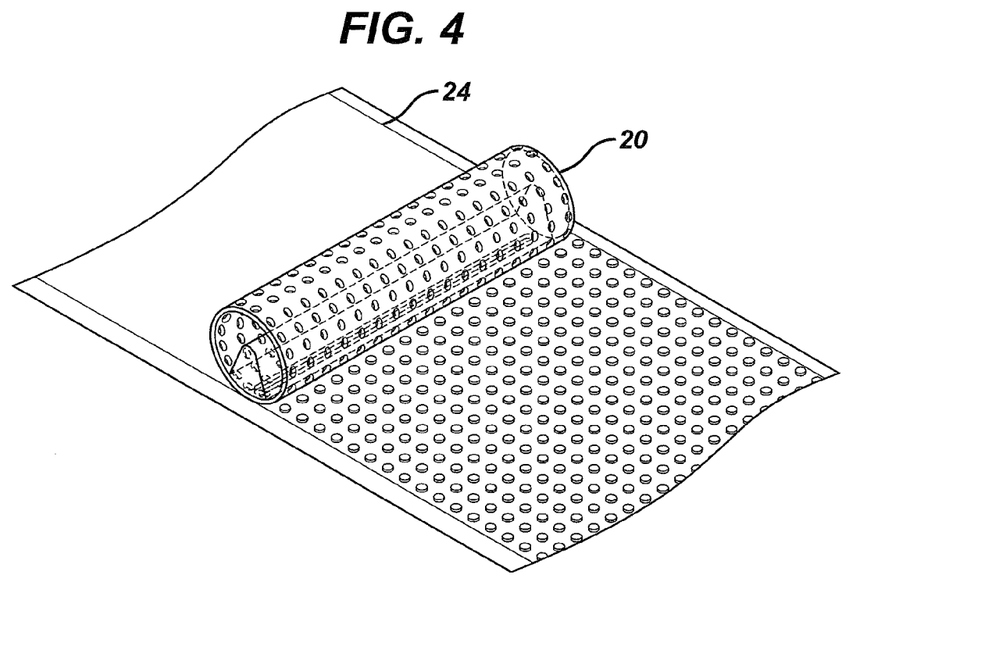
FIG. 4 shows a schematic view of a roller screen printing method according to the present invention.

A suitable roller method is shown in FIG. 3. In these embodiments, the roller 10 is formed having recesses 12 in its outer surface as hereinbefore described. The prepolymer is applied in a continuous layer to the outside surface of the intaglio roller 10 by a transfer roller 14. A doctor blade 16 wipes the outer surface of the intaglio roller leaving the apertures filled with the prepolymer. The coated roller is then applied to the moving substrate 18 to print the prepolymer onto the substrate 18, followed by curing.

In a third embodiment, the method of the present invention comprises providing a mold sheet having upper and lower surfaces and a pattern of apertures extending between the upper and lower surfaces, filling the apertures with the fluid silicone prepolymer composition, contacting one of said upper or lower surfaces with the support sheet so that said support sheet contacts said fluid silicone prepolymer composition in said apertures, curing the silicone prepolymer composition in contact with the support sheet, and removing the mold sheet. The step of curing may be carried out before or after the step of removing the mold sheet.

This method resembles screen printing, but the apertures in the mold sheet are substantially larger than the apertures in conventional printing screens so that the viscosity of the silicone precursor does not hinder printing. Suitably, the thickness of the mold sheet is from about 0.1 mm to about 2 mm, for example from about 0.2 mm to about 1 mm. The mold sheet may for example be a perforated metal sheet, a perforated plastic sheet, or a textile sheet having large apertures. The open area of the mold sheet is suitably from about 10% to about 90% of the total area, for example from about 10% to about 50% of the total area of the mold sheet.

Suitably, the apertures in the mold sheet are filled with the silicone adhesive prepolymer composition by flooding the mold sheet with prepolymer, followed by wiping excess prepolymer from the surfaces of the mold sheet, for example with a doctor blade. The step of flooding the mold sheet with prepolymer is suitably performed while one of the surfaces of the mold sheet is in contact with the substrate sheet.

Figure 5:
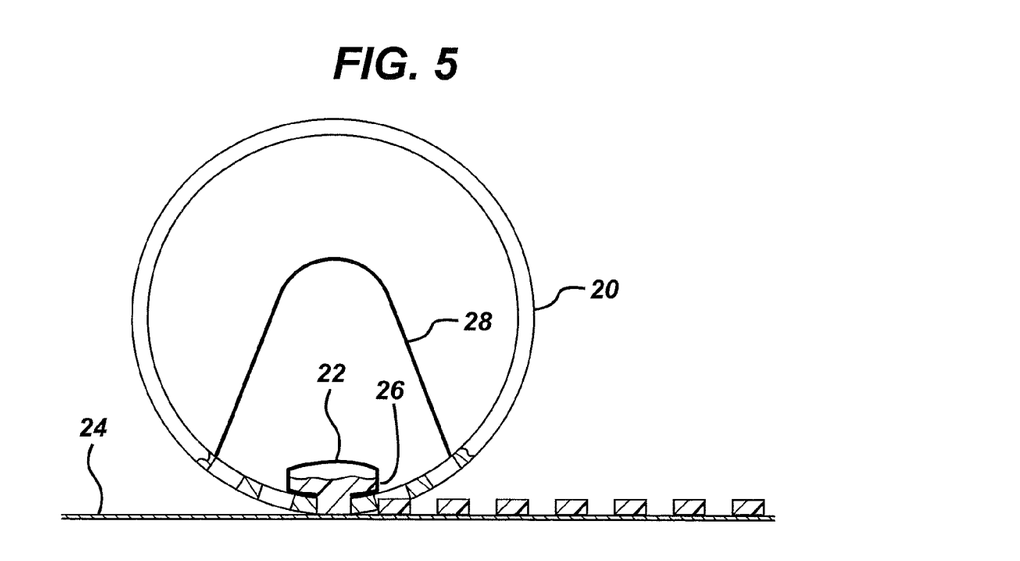
FIG. 5 shows a cross-section through the roller of FIG. 4.

The process may be carried out in discontinuous fashion using a plurality of flat mold sheets, or in continuous fashion using an apertured roller. A suitable roller method is shown in FIG. 5. In these embodiments, the screen printing roller 20 is formed from a mold sheet material as hereinbefore described. The prepolymer is pumped into channel 22 inside the roller so that it is fed selectively to the apertures of the roller 20 that are in contact with the substrate sheet 24. The position of the channel 22 is fixed as the roller rotates, so that one edge 26 of the channel acts as a doctor blade to wipe the inside surface of the roller after the apertures have been filled with the prepolymer. A concentric channel 28 may be provided that is fed with compressed air (or other compressed gas) to ensure that the prepolymer in the apertures is transferred to the substrate sheet 24 as the roller rotates. The printed substrate sheet is then cured.

In a second aspect, the present invention provides a substrate sheet having a patterned silicone adhesive coating thereon, obtainable by a method according to the present invention.

Figure 6:
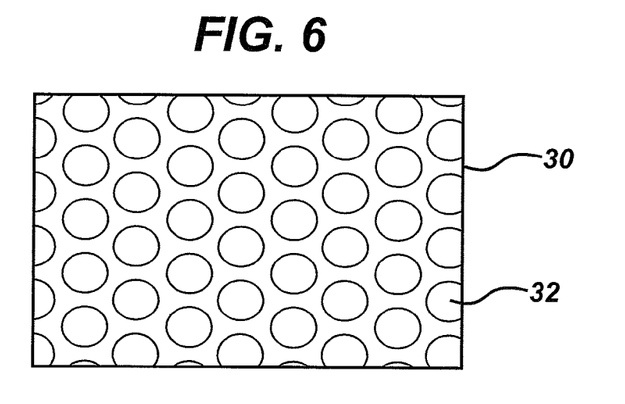
FIG. 6 shows a perspective view of a silicone-adhesive pattern coated substrate according to the present invention.

FIG. 6 shows a printed substrate sheet according to this aspect of the invention. The substrate 30 is a semipermeable polyurethane wound dressing backing sheet. The patterned silicone adhesive 32 is in the form of an open network of adhesive formed by block printing a mesh coated with the silicone prepolymer onto the substrate followed by curing. In other embodiments, the adhesive may be patterned as a continuous adhesive margin extending around the perimeter of the substrate sheet, whereby the central region of the substrate sheet is adhesive-free. The width of the adhesive coated margin is suitably from about 1 cm to about 4 cm. The adhesive-coated margin can then be used to attach the substrate sheet to skin surrounding a wound.

In a further aspect, the present invention provides a wound dressing comprising a substrate sheet according to the second aspect of the invention.

Suitably, the wound dressing according to the present invention is in the form of a piece having a total area of from about 1 cm$^2$ to about 1000 cm$^2$, for example from about 5 cm$^2$ to about 400 cm$^2$.

The dressing may comprise one or more releasable cover sheets over the adhesive pattern coated surface of the substrate to protect the adhesive surface before use. The cover sheets may comprise a film of polyethylene, polypropylene or fluorocarbons and papers coated with these materials. Suitably, the cover sheet is a release-coated paper sheet, such as a silicone release-coated paper sheet. Examples of silicone-coated release papers are POLYSLIK (Registered Trade Mark) supplied by H.P. Smith & Co., offered in various formulations to control the degree of adhesion of the paper to the silicone coated substrate surface.

In certain embodiments, the cover sheets may comprise two or more parts, such as a first removable part having a first edge and a second removable part that meets the first part along the first edge. Suitably, along each of said edges where the parts meet, one of the parts is folded back to provide a folded-back margin, and the other part overlaps the said folded-back margin. This provides an easy-to-grasp margin on each part in the region of overlap to assist removal of the cover sheet by the care giver. In other embodiments, the cover sheets may comprise three parts, for example as described in detail in EP-A-0117632.

Figure 7:
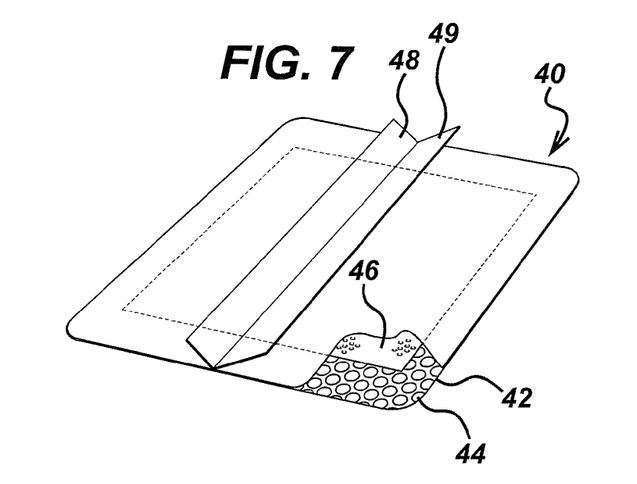
FIG. 7 shows a perspective view partially cut away of a wound dressing according to the present invention.

FIG. 7 shows a wound dressing according to this embodiment of the invention. The wound dressing 40 is an island-type dressing having a semipermeable polyurethane film backing sheet 42 that is the substrate for a printed pattern 44 of silicone adhesive. An absorbent island 46 of hydrophilic polyurethane foam is adhered centrally on the backing sheet by the silicone adhesive. Release coated cover sheets 48,49 are applied over the wound facing side of the dressing.

Figure 8:
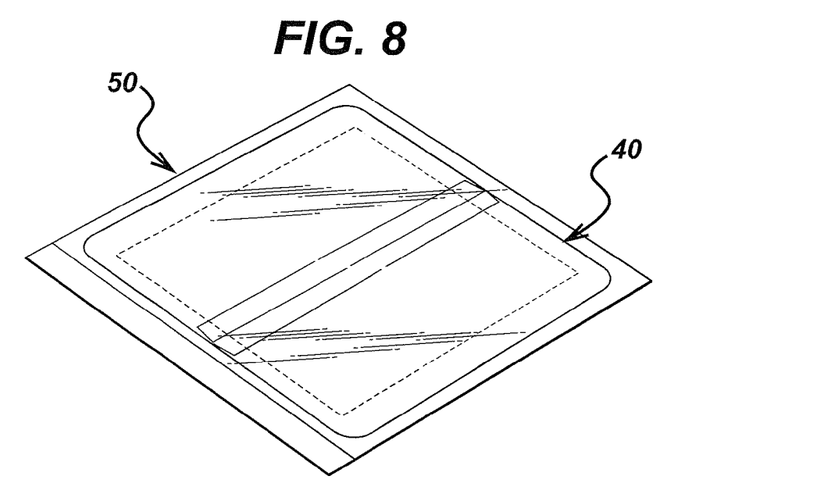
FIG. 8 shows the wound dressing of FIG. 7 packaged in a microorganism-impermeable container.

Suitably, the wound dressings of the invention are sterile and packaged in a microorganism-impermeable container, such as a pouch. FIG. 8 shows the wound dressing 40 of FIG. 7 packaged in a microorganism-impermeable pouch 50.

Any feature disclosed herein in relation to any one or more aspects of the invention may be present in any of the other aspects defined herein. Likewise, any combination of the alternative features described herein may be present in any of the aspects of the invention. It will be understood that all such combinations and features of the different aspects have not been described in detail herein solely for reasons of brevity.

EXAMPLE 1

A support mesh is coated with a fluid silicone adhesive prepolymer composition. The support mesh is a polypropylene sheet having a hexagonal (close packed) array of circular apertures of diameter 8 mm and open area about 60%. The silicone prepolymer is made by mixing Components Gel A and Gel B (Dow Corning products Q7-9177) at a weight ratio of 50:50 at 25-40° C. The mesh is coated by transferring of mixture using either a roller or a coating machine.

The silicone prepolymer composition on the support mesh is gently pressed onto substrate sheet formed of 0.4 mm high-density polyurethane foam formed from a blocked toluene di-isocyanate. The coated substrate with the mesh in place is then cured at 110-150° C. for 2 to 6 minutes. The support mesh is then lifted off to leave a pattern of adhesive on the support sheet corresponding to the pattern of lands on the support mesh This results in a substrate coated with a patterned silicone adhesive as shown in FIG. 6.

Moisture vapour transfer rate (MVTR) was measured for the resulting pattern coated adhesive sheets. For comparison, MVTR was also measured for the semipermeable substrate layer without any coating, and for the semipermeable substrate layer having a continuous coating of the same silicone adhesive. The results were as follows:

| Material | MVTR (g/m$^2$/24 hr) |
| --- | --- |
| Film Backing | 12002.5 |
| Film backing + continuous layer of silicone | 311 |
| Film backing + patterned layer of silicone | 8910.5 |

It can be seen that the silicone adhesive is substantially impermeable to moisture, but that this drawback can be substantially overcome by the use of the patterned adhesive coating.

EXAMPLE 2

The method of Example 1 is repeated with replacement of the semipermeable film substrate by a hydrophilic polyurethane foam substrate (TIELLE®, produced by Systagenix Wound Management). A similar printed adhesive pattern is achieved on the foam.

The above examples have been described by way of illustration only. Many other embodiments falling within the scope of the accompanying claims will be apparent to the skilled reader.

The invention claimed is:

1. A method of applying a patterned coating of a silicone adhesive to a substrate sheet, comprising the steps of pattern coating a silicone precursor composition onto at least a portion of the substrate sheet, followed by thermally curing the precursor composition coated on the portion of the substrate sheet, wherein the step of pattern coating comprises the steps of coating the silicone precursor composition onto an apertured support layer to provide a coated apertured support layer, followed by applying the coated apertured support layer to the substrate sheet, followed by thermally curing the silicone precursor composition, followed by removing the coated apertured support layer to leave a patterned layer of the cured silicone composition on the substrate sheet, whereby the pattern of the cured silicone on the substrate sheet substantially corresponds to a pattern of coating on the apertured support layer.

2. A method according to claim 1, wherein the pattern of coating is formed by a pattern of lands and holes in the support layer.

3. A method according to claim 1, wherein said apertured support layer is a perforated sheet containing an array of perforations, said perforations having an area of at least about 4 mm$^2$.

4. A method according to claim 1, wherein the silicone precursor composition is substantially solvent-free.

5. A method according to claim 1, wherein said pattern coating of silicone precursor composition is applied to cover from about 10% to about 50% of the surface area of the substrate sheet.

6. A method according to claim 1, wherein said coating of silicone adhesive precursor composition is applied in a pattern having a minimum dimension of about 2 mm.

7. A method according to claim 1, wherein said substrate sheet is a continuous semipermeable sheet having a moisture vapour transfer rate (MVTR) before coating of at least about 500 g/m$^2$/24 hr.

8. A method according to claim 1, wherein no primer layer is applied to said substrate sheet prior to said step of pattern coating with the silicone precursor composition.

9. A method according to claim 1, wherein the support layer has a surface that substantially comprises a perfluorocarbon.

* * * * *

UNITED STATES PATENT AND TRADEMARK OFFICE
CERTIFICATE OF CORRECTION

| | | |
|---|---|---|
| PATENT NO. | : 9,433,534 B2 | |
| APPLICATION NO. | : 14/111626 | |
| DATED | : September 6, 2016 | |
| INVENTOR(S) | : Deborah Addison | |

It is certified that error appears in the above-identified patent and that said Letters Patent is hereby corrected as shown below:

In the Claims

At Column 12, Claim number 6, Line number 32, delete "adhesive"

Signed and Sealed this
Seventh Day of February, 2017

Michelle K. Lee
*Director of the United States Patent and Trademark Office*